United States Patent [19]

Ritter

[11] 4,146,609

[45] Mar. 27, 1979

[54] TRAIL-FOLLOWING SUBSTANCE

[75] Inventor: Fridolin J. Ritter, Waddinxveen, Netherlands

[73] Assignee: Nederlandse Organisatie Voor Toegepastnatuurwetenschappelijk Onderzoek Ten Behoeve Van Nijverheid, Handel en Verkeer, The Hague, Netherlands

[21] Appl. No.: 876,611

[22] Filed: Feb. 10, 1978

[30] Foreign Application Priority Data

Feb. 14, 1977 [GB] United Kingdom ............... 6086/77

[51] Int. Cl.$^2$ ........................................... A01N 17/14
[52] U.S. Cl. .................................................. 424/84
[58] Field of Search ........................................ 424/84

[56] References Cited

FOREIGN PATENT DOCUMENTS 2528656 1/1976 Fed. Rep. of Germany.
1434057 4/1976 United Kingdom.

*Primary Examiner*—Donald B. Moyer
*Attorney, Agent, or Firm*—Brumbaugh, Graves, Donohue & Raymond

[57] ABSTRACT

Substances which induce trail-following in ants characterized by the formula (6E,10Z)-3,4,7,11-tetramethyl-6,10-tridecadienal-1, methods for preparing said compounds, and a lure composition comprising said compounds.

4 Claims, No Drawings

TRAIL-FOLLOWING SUBSTANCE

This invention relates to substances which induce trail-following in ants and which can be used to lure these insects towards baits or other devices for controlling or eradicating insects.

The use of substances to lure insects into a situation in which they can be killed or rendered harmless is known. One method of doing this is to lure the insects into a particular location and then cause contact between the insects and an insecticide, insect hormone or insect pathogen. In such a case there is no need to disperse the insecticide widely and indiscriminately over large areas, but instead the combination of pesticide and luring trail-following substances can be placed either as a mixture or as closely spaced quantities, in the neighborhood of those places which have to be protected against the harmful influence of the insects.

A further method is to use the trail-following lure substance in combinations with a trap; the insects may be killed in this trap or may stick fast to a glue on the walls of the trap. These and other methods for using lures for controlling insects are known and can be used in accordance with the present invention.

Another important application of trail-following lures is to signal the presence, distribution and spread of the insect. Its presence thus can be detected in good time to take the necessary steps for control, and it will not be necessary to wait until the insect manifests itself as a pest by its presence in large numbers or by having caused damage. In addition the lure might render unnecessary the preventive use of pesticides outside the period of presence of the insects. Moreover, through use of the trail-following lure a much more definite picture of the extent and intensity of an infestation can be obtained. Thus, plans for containment are more feasible and control efforts can be directed more precisely.

Ants, such as the Pharaoh's ant, are in many places a great danger to public health and are often very hard to control. Especially in buildings with central heating, in bakeries and laundries, but also in private houses they form a great problem. The Pharaoh's ant has been shown to be a major carrier of human pathogenic micro-organisms in many hospitals (Susan H. Beatson, The Lancet, Feb. 19, 1972, p. 425: "Pharoah's ants as pathogen vectors in hospitals"). In such places, where the use of toxic substances has to be avoided as much as possible, lures can be of great importance.

In our U.K. patent specification No. 1,434,057, published Apr. 28, 1976, and in the pending U.K. patent application No. 27281/75 (= German patent application No. 2,528,656) of the same applicant, new and powerful attractant agents for ants, such as the Pharaoh's ant (*Monomorium pharaonis* L) are described, viz, 5-methyl-3-n-butyl-octahydroindolizine and 2-(5'-n-hexenyl)-5-n-pentylpyrrolidine respectively.

A novel and powerful substance that induces trail-following in ants of the genus Monomorium, such as *Monomorium pharaonis* (L.) (the Pharaoh's ant) and *Monomorium floricola* (Jerdon) is (6 E, 10 Z)-3,4,7,11-tetramethyl-6,10-tridecadienal-1. (I).

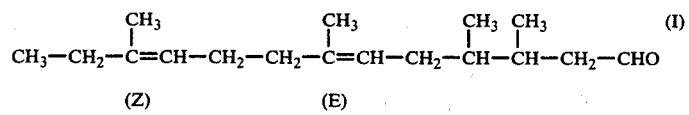

This very active compound I can be obtained by a Wittig reaction from (Z)-5-methyl-4-heptenyltriphenylphosphonium iodide (II) and the monoacetal of 3,4-dimethyladipaldehyde, which is 6,6-diethoxy-3,4-dimethylhexanal (III) (E and Z denoting trans and cis configurations, respectively).

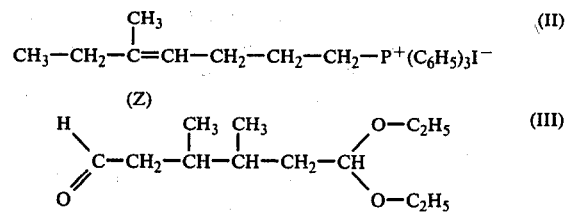

Compound (I) can be synthesized from compounds (II) and (III) by a reaction similar to that described by E. J. Corey and H. Yamamoto, J. Am. Chem. Soc. 92, 6636–6637 (1970) for the synthesis of a juvenile hormone. The synthesis of compound II has been described by E. J. Corey, H. Yamamoto, D. K. Herron and K. Achiwa, J. Am. Chem. Soc., 92, 6635–6636 (1970).

Compound III can be obtained from 1,2-dimethyl-4-cyclohexene by ozonolysis at a low temperature. Reduction of the ozonide with dimethyl sulphide to 3,4-dimethyladipaldehyde, followed by in situ acetalisation with triethyl orthoformate of the dialdehyde, yields 1,1,6,6-tetraethoxy-3,4-dimethylhexane.

Partial hydrolysis in an acidic medium of the tetraethoxy compound yields III. The reaction scheme of the formation of I from II and III is as follows:

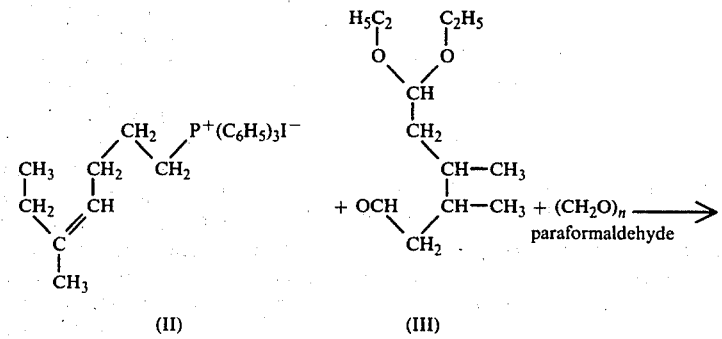

-continued

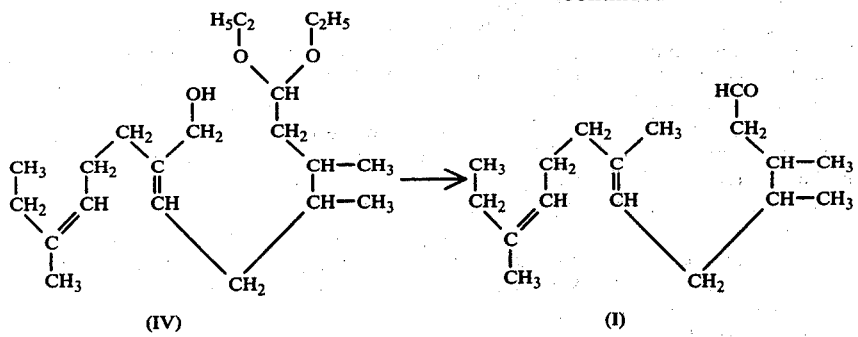

It has been found that the compound specified is a very potent trail-following agent, for ants, particularly those of the genus Monomorium.

When slow-acting insecticides, insect hormones, hormone mimics, or insect pathogens, or insect sterilants are present at the end of a trail of compound (I) or at any other spot on this trail, the ants can still return to the place from whence they came (the nest), but in doing so they contaminate the nest with the insecticide or other control agent. In particular, worker ants can in this way transmit the control agent to the queen and the larvae, which enhances the value of this control method. In addition, when returning from a place where compound (I) and the control agent are located, the insects may contaminate themselves with the compound, leaving a trail of it that is preferentially followed by other ants to the place where compound (I) and the control agent are located.

Since the effective amounts of compound (I) are extremely small, it is preferably handled in combination with a fluid or solid carrier. The substance described in the present invention can also be present in a closed space, the walls of which are permeable to the vapor of compound (I), such as a capsule of a suitable plastic material.

Substances toxic to ants can be added to preparations containing compound (I). It is also possible to apply compound (I) to or inside a sticky surface capable of immobilizing the ants, so that they can be disposed of. Such means are known in the art.

Compound (I) can also be used to improve the effectiveness of a bait that contains foodstuffs for the animals, such as products which contain proteins (liver or meat, fresh or dried), sugar, honey or the like, or which contain water or a suitable product containing water.

Preparations which, in addition to compound (I), also contain the compounds mentioned above and described in the applicant's previous U.K. patent specification No. 1,434,057 and in U.K. application No. 27281/75, viz, 5-methyl-3-n-butyl-octahydroindolizine and 2-(5'-n-hexenyl)-5-n-pentylpyrrolidine, respectively, are particularly useful, because they possess a mutually synergistic action.

EXAMPLE I

Synthesis and physical properties of (6E, 10Z)-3,4,7,11-tetramethyl-6,10-tridecadienal-1 (I)

(Z)-5-Methyl-4-heptenyltriphenylphosphonium iodide (II), is prepared by methods generally known in the art (and described in the literature mentioned above).

6,6-Diethoxy-3,4-dimethylhexanal (III) is synthesized in the following way:

A solution of 0.05 mol of 1,2-dimethyl-4-cyclohexene in 200 ml of ethanol is cooled to −70° C. Ozonized oxygen gas is passed through the solution at a rate of 20 l/hr until one molar equivalent of ozone has been absorbed. While still at −70° C., the system is flashed with nitrogen and a mixture of 0.08 mol of dimethyl sulphide, 0.49 mol of triethyl orthoformate and 10 ml of methanol containing 0.08 mol of HCl/l is added. The solution is stirred and allowed to warm up from −70° C. to +20° C. in 12 hrs. The hydrogen chloride is neutralized with dry sodium hydrogen carbonate, and the solvent removed by distillation.

The residue is dissolved in 120 ml of dry tetrahydrofuran (THF) to which 3.6 ml of water and 1.2 ml of a 10% HCl solution are added. After standing for 45 minutes, the solution is neutralized by addition of sodium hydrogen carbonate.

The solution is then filtered, and the solvent removed at reduced pressure (20 mm Hg), afhter which the residue is distilled through a "Mikro Spaltrohr" column.

About 0.02 mol of III (b.p. 110° C./5 mm Hg) is thus obtained.

A solution of 10 mmoles of (II), m.p. 178° C., in dry THF is reacted with 10 mmoles of n-butyllithium for 30 min. at 0° C., so that compound (II) is converted into the corresponding ylide. The solution is cooled to −78° C., and allowed to react with 10 mmoles of (III) for 5 min. upon which the solution is warmed to 25° C., and treated with 20 mmoles of sec-butyllithium (1.20 M in pentane) for 5 min. The deep red solution is then brought to 0° C., and after addition of 30 mmoles of dry paraformaldehyde, the resulting mixture is stirred for 30 min. at 25° C. To this mixture water is added and after extraction and chromatographic separation to remove the triphenylphosphine oxide formed, the unsaturated alcohol-acetal (IV) is obtained (4 mmoles).

One-and-a-half mmol of the complex of pyridine and sulphur trioxide is added at −5° C. to a solution of 1 mmol of IV in 10 ml of THF. The resulting suspension is stirred and allowed to warm up from −5° C. to 0° C. in 5 hrs. A solution of 6 mmol of LiAlH₄ in 10 ml of THF is added at 0° C., and the mixture stirred at 0° C. for 1 hr and at 25° C. for 3 hrs. Upon addition at 0° C. of 0.20 ml of water, 0.25 ml of a 15% aqueous sodium hydroxide solution, and 0.7 ml of water to the solution, 40 ml of ether is added, and the precipitate that has formed is filtered off and washed with ether.

The solution is acidified with dilute sulphuric acid and stirred for 30 minutes.

The organic layer is separated and dried over anhydrous sodium sulphate. Removal of the solvent by distillation leaves behind 0.4 mmol of I. After removal of the solvent by distillation, 0.54 mmoles of (I) are obtained. It is purified by gas chromatography at 170° C. on a 2m-column of 10% Carbowax-20 M on Chromosorb W (acid-washed), with nitrogen (35 ml per minute) as the mobile phase. The fraction appearing as a peak of Kovàts retention index (see. Anal. Chem. Vol. 36, Nr. 8, 1409 -July 1964) 2130 was collected. It showed the following characteristic properties:

Kovàts retention index in gas chromatography: 2345, 2130, 2120, 1910, 1790, and 1780 on columns with the stationary phases DEGS, Carbowax-20 M, OV-225, OV-17, OV-101, and SE-30 + 5% Carbowax-20 M respectively.

Mass spectrum: main peaks (with relative intensities at m/e 250 (2) (parent peak corresponding to the molecular formula $C_{17}H_{30}O$); 203 (2); 193 (13); 137 (11); 123 (17); 107 (13); 95 (16); 83 (88); 55 (100) and 41 (35).

Infrared spectrum: bands at 2970 to 2850; 2820; 2710; 1727; 1375 cm−1. NMR spectrum in carbon disulphide: (in ppm) 0.81 (3 H, doublet-J=7 Hz); 0.895 (3 H, doublet, J=6.5 Hz); 0.925 (3 H, triplet-J=7.5 Hz); 1.54 (3 H, broadened singlet); 1.61 (3 H, broadened singlet); about 1.4–2.3 (12 H, multiplets, of which 9 H at 1.9–2.1); 4.95 (1 H, triplet J=7 Hz, broadened); 5.02 (1 H, triplet, J=7 Hz, broadened); 9.64 (1 H, broadened singlet).

These data are in agreement with those expected for structure (I).

EXAMPLE II

Biological properties of (6E, 10Z)-3,4,7,11-tetramethyl-6,10-tridecadienal-1(compound I)

Under laboratory conditions amounts of $10^{-2}$ to $10^{-7}$g of compound (I) per location (a paper strip of 10 × 0.4 cm) gave significant results in selected tests with Pharaoh's ants when compared with controls not containing compound (I). Very significant results were obtained with amounts of $10^{-9}$g per location.

When $10^{-11}$ to $10^{-7}$g of compound (I) of the invention are applied as a thin circle having a perimeter of 47 cm, that is to say, in an amount of $0.2 \times 10^{-12}$ to $0.2 \times 10^{-8}$g/cm, workers as well as queens and males of *Monomorium pharaonis* (L.), the Pharaoh's ant, followed the trail of the circle. Similar experiments with workers of a related species, *Monomorium floricola* (Jerdon) followed trails of the same concentration. In this test, compound (I) was applied as a solution in hexane.

In a laboratory experiment with queens of the Pharaoh's ant, the insects, for some time, following a thin circle as described above and having a concentration of $0.2 \times 10^{-11}$g/cm. After about 10 min., they clustered together at one point of the circle. This aggregation is an important phenomenon in the application of the compound.

The possibility of luring queens towards particular locations by means of substance (I) is of major importance for the control of the insect, because it is the queens that must be killed if further reproduction is to be prevented.

The ability of compound (I) to lure worker ants, however, is also important. When all worker ants are prevented from returning to the nest after having been lured towards a certain location, the supply of nutrients to the nest is stopped, and the larvae and remaining queens will die of starvation. As mentioned before, it is also possible to contaminate the workers with control agents, so that, on returning the nest, they will contaminate the entire nest, including the reproductive insects (queens and males), and the larvae, pupae and eggs, whereby the entire population is exterminated. Particularly for ants, such as the Pharaoh's ant, the nests of which are hard to find, these methods are of great importance as selective and effective control methods.

The effect of compound (I) is strenghened when (I) is combined with the compounds described in U.K. patent specification No. 1,434,057, and/or in U.K. application No. 27281/75. When, for example, a mixture containing $8 \times 10^{-11}$g of 2-(5'-n-hexenyl)-5-n-pentylpyrrolidine, $3 \times 10^{-11}$g of 5-methyl-3-n-butyl-octahydroindolizine, and $2 \times 10^{-12}$g of compound (I) were applied in a thin circle as described above, workers as well as queens of the Pharoch's ant followed it for a considerable time.

EXAMPLE III

Semi-technical experiment with a bait, and with paper strips containing compound (I)

A laboratory colony of Pharaoh's ants, containing worker ants, queens, males, pupae, larvae and eggs was reared as described in the literature (A. Buschinger and M. Petersen, Anzeiger Schädlingskunde, 44, 103 (1071)). To the plastic box (measuring about 22 × 14 × 18 cm) which housed the insect colony, two Y-shaped glass tubes were connected at opposite sides. The length of the lower parts of the Y-tubes was 4 cm, and the length of the two upper parts 17 cm: the inner diameter of the tubes was 0.8 cm. The two upper legs of the Y-shaped tubes were connected to a small glass vessel containing about 250 mg dry dog's food. Before the tubes were connected to the plastic rearing-box, paper strips of 15 × 0.4 cm were placed in each of the upper legs of the Y-shaped devices, one strip containing $10^{-9}$g of compound (I), and the other being blank.

It soon appeared that the ants preferentially followed the route to the bait in the vessels connected to those legs which contained compound (I). Over a 20 min. period the ants in each vessel were counted 5 minutes. The total scores were 40 and 51 for compound (I), as against 5 and 0 for the blanks. Most of the insects were worker ants, but a few queens were also seen. This experiment shows that very small amounts of compound (I) can be used effectively for luring Pharaoh's ants towards baits and into traps.

EXAMPLE IV

Extermination of Pharoah's ants in practice

In a building where Pharaoh's ants constituted a serious pest, an experiment was conducted for the purpose of determining the usefulness of compound (I) in exterminating the insect pest.

Baits were made from a dry powder containing dog's food, liver, and 0.2% of "chlorodecone," which is decachloropentacyclo$(3,3,2,0^{2,6},0^{3,9},0^{7,10})$decane-4-one. A part of this bait was mixed homogeneously with 0.2 ppm ($2 \times 10^{-7}$g per g) of compound (I). Portions of 1 gram of baits with and without compound (I) were placed in small glass tubes that were attached to the walls in various parts of the building. A total of 42 tubes with and 36 tubes without compound (I) were distributed in the building, in five dwellings where the ants had been observed. It was seen almost immediately that the ants were by preference visiting the baits containing compound (I), many fewer of them visiting the adjoining baits without the compound.

An inspection after one week, of the five dwellings revealed that the ants had disappeared from four of them, and had strongly declined in number in the fifth. A second inspection, 2½ weeks later, showed that the ants had been virtually exterminated, the few workers (and queens!) still observed moving very sluggishly. Shortly afterwards these had also disappeared.

The time needed for complete extermination of the pest in this experiment was short in comparison with the duration of control experiments carried out elsewhere, and in which only baits without compound (I) were used. In the latter experiments, the time needed to eradicate the pest was several months.

I claim:

1. A lure or bait composition, having trail following properties comprising as the active ingredient an effective amount of the compound (6E,10Z)-3,4,7,11-tetramethyl-6,10-tridecadienal-1 and a suitable carrier.

2. A lure or bait composition according to claim 1 further comprising the compound 2-(5'-n-hexenyl)-5-n-pentylpyrrolidine.

3. A lure or bait composition according to claim 1 further comprising the compound 5-methyl-3-n-butyloctahydroindolizine.

4. A lure or bait composition according to claim 1 further comprising a mixture of the compounds 2-(5'-n-hexenyl)-5-n-pentyl-pyrrolidine and 5-methyl-3-n-butyl-octahydroindolizine.

* * * * *

UNITED STATES PATENT AND TRADEMARK OFFICE
CERTIFICATE OF CORRECTION

PATENT NO. : 4,146,609
DATED : March 27, 1979
INVENTOR(S) : Fridolin J. Ritter

It is certified that error appears in the above-identified patent and that said Letters Patent are hereby corrected as shown below:

Column 1, line 23, "substances" should read -- substance --;
line 28, "combinations" should read -- combination --;
line 53, "Pharoah's" should read -- Pharaoh's --;
Column 4, line 25, "HCl/1" should read -- HCL/1 --;
line 32, "HCl" should read -- HCL --;
Column 5, line 15, "intensities" should read -- intensities) --;
line 20, "NMR spectrum..." should start a new line;
line 34, "$10^{-2}$" should read -- $10^{-12}$ --;
line 50, "following" should read -- followed --;
line 68, after "returning" insert -- to --;
Column 6, line 15, "Pharoch's" should read -- Pharaoh's --.

Signed and Sealed this

Thirtieth Day of October 1979

[SEAL]

Attest:

RUTH C. MASON
Attesting Officer

LUTRELLE F. PARKER
Acting Commissioner of Patents and Trademarks